(12) United States Patent
Davidoff (10) Patent No.: US 11,406,713 B2
(45) Date of Patent: Aug. 9, 2022

(54) XANTHINE OXIDASE INHIBITOR FORMULATIONS

(71) Applicant: Allen Davidoff, Calgary (CA)

(72) Inventor: Allen Davidoff, Calgary (CA)

(73) Assignee: XORTX THERAPEUTICS, INC., Alberta (CA)

( * ) Notice: Subject to any disclaimer, the term of this patent is extended or adjusted under 35 U.S.C. 154(b) by 0 days.

(21) Appl. No.: 14/776,905

(22) PCT Filed: Mar. 17, 2014

(86) PCT No.: PCT/IB2014/001042
§ 371 (c)(1),
(2) Date: Sep. 15, 2015

(87) PCT Pub. No.: WO2014/140868
PCT Pub. Date: Sep. 18, 2014

(65) Prior Publication Data
US 2016/0038595 A1    Feb. 11, 2016

Related U.S. Application Data (60) Provisional application No. 61/790,414, filed on Mar. 15, 2013.

(51) Int. Cl.
| | | |
|---|---|---|
| *A61K 31/519* | (2006.01) | |
| *A61K 47/18* | (2017.01) | |
| *A61K 9/14* | (2006.01) | |
| *A61K 9/19* | (2006.01) | |
| *A61K 9/00* | (2006.01) | |
| *A61K 31/375* | (2006.01) | |
| *A61K 31/4188* | (2006.01) | |
| *A61K 31/4415* | (2006.01) | |
| *A61K 31/714* | (2006.01) | |
| *A61K 31/455* | (2006.01) | |
| *A61K 31/525* | (2006.01) | |
| *A61K 31/51* | (2006.01) | |
| *A61K 31/593* | (2006.01) | |
| *A61K 31/197* | (2006.01) | |
| *A61K 31/198* | (2006.01) | |
| *A61J 1/00* | (2006.01) | |

(52) U.S. Cl.
CPC ........... *A61K 47/183* (2013.01); *A61J 1/00* (2013.01); *A61K 9/0095* (2013.01); *A61K 9/14* (2013.01); *A61K 9/19* (2013.01); *A61K 31/197* (2013.01); *A61K 31/198* (2013.01); *A61K 31/375* (2013.01); *A61K 31/4188* (2013.01); *A61K 31/4415* (2013.01); *A61K 31/455* (2013.01); *A61K 31/51* (2013.01); *A61K 31/519* (2013.01); *A61K 31/525* (2013.01); *A61K 31/593* (2013.01); *A61K 31/714* (2013.01)

(58) Field of Classification Search
None
See application file for complete search history.

(56) References Cited

U.S. PATENT DOCUMENTS

| | | | | |
|---|---|---|---|---|
| 3,624,205 A | * | 11/1971 | Hitchings | A61K 31/505 514/262.1 |
| 3,689,641 A | * | 9/1972 | Spangler | A21D 2/08 424/648 |
| 5,211,956 A | * | 5/1993 | Sawai | A61K 31/66 424/451 |
| 5,272,151 A | * | 12/1993 | Marzi | C07K 5/06026 514/21.8 |
| 5,484,605 A | | 1/1996 | Scheiffele | |
| 5,661,154 A | | 8/1997 | Scheiffele | |
| 6,264,981 B1 | * | 7/2001 | Zhang | A61K 9/0056 424/451 |
| 6,544,726 B1 | | 4/2003 | Van Dyke et al. | |
| 6,569,862 B1 | | 5/2003 | Marban | |
| 2003/0049840 A1 | * | 3/2003 | Demetriou | A01N 1/02 435/404 |
| 2004/0258748 A1 | * | 12/2004 | Madan | A61K 9/0007 424/464 |
| 2006/0141076 A1 | * | 6/2006 | Palu | A61K 36/45 424/732 |
| 2010/0137284 A1 | * | 6/2010 | Stamler | A61K 31/047 514/212.07 |
| 2015/0353471 A1 | * | 12/2015 | Chen | C07C 205/37 514/63 |
| 2016/0051602 A1 | * | 2/2016 | Chen | A61K 35/747 424/115 |

FOREIGN PATENT DOCUMENTS

| | | |
|---|---|---|
| CA | 2519126 | 9/2004 |
| CN | 102372679 A * | 3/2012 |

(Continued)

OTHER PUBLICATIONS

Rowe, Methylcellulose, Handbook of Pharmaceutical Excipients, 2003, Pharmacuetical Press, 386-389.*
Muraoka et al., Inhibition of xanthine oxidase by phytic acid and its antioxidative action, Life Sci. Feb. 13, 2004;74(13):1691-700, printed from https://www.ncbi.nlm.nih.gov/pubmed/14738912, 2 pages, Abstract only.*
Warner, Vitamin C May Help Prevent Gout, www.webmd.com/arthritis/news, Mar. 9, 2009, printed from http://www.webmd.com/arthritis/news/20090309/vitamin-c-may-help-prevent-gout, 5 pages.*
Atteia et al., Antioxidant activity of folic acid: From mechanism of action to clinical application, Apr. 1, 2009, The FASEB Journal 2009 23:1_supplement, 103.7-103.7 , printed from https://www.fasebj.org/doi/abs/10.1096/fasebj.23.1_supplement.103.7, Abstract only, 2 pages.*

(Continued)

*Primary Examiner* — Gigi G Huang
(74) *Attorney, Agent, or Firm* — Timothy H. Van Dyke; Wolter, Van Dyke, Davis, PLLC (57) ABSTRACT

Disclosed herein are methods and compositions for involving a xanthine oxidase inhibitor that has enhanced solubility. The compositions described herein include a xanthine oxidase inhibitor combined with an organic base. The compositions can be used to treat a disease or medical condition that involves elevated uric acid levels.

11 Claims, 2 Drawing Sheets

(56) References Cited

FOREIGN PATENT DOCUMENTS

| CN | 102641255 A | * | 8/2012 | |
|---|---|---|---|---|
| WO | 2006083687 A1 | | 8/2006 | |
| WO | 2007044910 A1 | | 4/2007 | |
| WO | 2011097269 A9 | | 8/2011 | |
| WO | WO 2011101867 A2 | * | 8/2011 | ........... C07D 277/56 |
| WO | 2012098501 A1 | | 7/2012 | |

OTHER PUBLICATIONS

Barrows et al., Color Additives History, Food Safety Magazine, Oct./Nov. 2003, printed from https://www.fda.gov/industry/color-additives/color-additives-history#authors, 13 pages.*

Ohno et al., Asimple freezing medium for serum-free cultured cells, Cytotechnology. Jul. 1988;1(3):257-60, printed from https://www.ncbi.nlm.nih.gov/pubmed/22359122, 1 page, Abstract only.*

Ishihara et al., Intake of folate, vitamin B6 and vitamin B12 and the riskof CHD: the Japan Public Health Center-Based Prospective Study Cohort I, J Am Coll Nutr. Feb. 2008;27(1):127-36, printed from https://www.ncbi.nlm.nih.gov/pubmed/18460491, 1 page, Abstract only.*

Choi et al., Vitamin C intake and the riskof gout in men: a prospective study, Arch Intern Med. Mar. 9, 2009;169(5):502-7, printed from https://www.ncbi.nlm.nih.gov/pubmed/19273781, 2 pages, Abstract only.*

Lieberman et al., Pharmaceutical Dosage Forms:Tablets—Colorants, 1989, Marcel Dekker, pp. 116-117.*

Lieberman et al., Pharmaceutical Dosage Forms:Tablets—Binders and Adhesives, 1989, Marcel Dekker, pp. 105-108.*

Moorhouse et al., Allopurinol and oxypurinol are hydroxyl radical scavengers, FEBS Lett. Mar. 9, 1987;213(1):23-8, printed from https://www.ncbi.nlm.nih.gov/pubmed/3030809, Abstract only, 1 page.*

PCT/IB2014/001042; International Search Report and Written Opinion, dated Sep. 18, 2014, 11 pages.

Ammar, H.O. et al., "Solubilization of allopurinol with methyl xanthines", J. Phys Chem, Apr. 2005, abstract only.

Hirano, Atsushi et al., "Arginine-Assisted Solubilization System for Drub Substances: Solubility Experiment and Simulation", Journal of Physical Chemistry B, Oct. 2010, vol. 114, No. 42, pp. 13455-13462.

EP Search Report for EP14764884.4; dated Jun. 21, 2019; 6 pages.

"NDA 21-740-OXYPRIM" Arthritis Advisory Committee Briefing Documents; Jun. 2, 2004, 14 pages.

* cited by examiner

XANTHINE OXIDASE INHIBITOR FORMULATIONS

CROSS-REFERENCE TO RELATED APPLICATIONS

This application claims priority to and incorporates by reference the contents of Provisional Application No. 61/790,414 filed on Mar. 15, 2013 under 35 USC 119.

BACKGROUND

Chronically increased serum uric acid has been associated with pathophysiology of gout, hypertension (1), metabolic syndrome and diabetes (2) and kidney disease (3). Similarly, increased serum uric acid has been associated with both decreased nitric oxide bioavailability (4) and increased production of oxygen free radicals (5). Uric acid is virtually insoluble in water or common organic solvents, but it can be dissolved in a basic solution such as aqueous solutions of Li2CO3 (6), KOH (7), NaOH(8), and ammonium hydroxide (9).

Historically, Xanthine Oxidase Inhibitors (XOI) for the treatment of gout and hyperuricemia (U.S. Pat. No. 5,484,605), have been delivered in tablet form. These compounds have been reported to be useful in treating excessive resorption of bone (U.S. Pat. No. 5,674,887). Two Xanthine oxidase inhibitors: Allopurinol, and oxypurinol are poorly soluble and poorly bioavailable, resulting in the development of formulations specifically developed to treat gout or cancer, address this problem. Compositions containing allopurinol and oxypurinol have been formulated to enhance resorption of the compounds in the treatment of gout and chronic inflammatory intestinal diseases or in the setting of cancer. Such compositions include oral dosage forms of oxypurinol alkali or alkaline earth salts, in an amorphous or crystalline, non-micronized state; and oxypurinol or its alkali or alkaline earth salts in the form of a solids dispersion with pharmacologically inert adjuvants. (U.S. Pat. Nos. 5,661,154 and 5,368,864). The citation of any reference herein is not an admission that such reference is available as prior art to the instant invention.

SUMMARY

The applicants were able to demonstrate increased equilibrium solubility, increased dissolution rate and solubility of XOI and more specifically of oxypurinol using organic and or basic organic molecules, in aqueous solutions compared to oxypurinol free acid.

Disclosed herein are novel formulations of xanthine oxidase inhibitors with organic bases, especially liquid formulations and formulations that enhance the equilibrium solubility, overall solubility and dissolution of xanthine oxidase inhibitors in the presence of solvents. These formulations can provide advantageous methods of treatment or protection (e.g. prevention of a condition or disease due to hyperuricemia) of subjects (patient or animal) by demonstrating improved chemical, biological, and/or physical properties compared to formulations comprising only a xanthine oxidase inhibitor. Thus, the formulations may address the need for more efficacious dosage forms for xanthine oxidase inhibitors. Demonstrated here are properties of the invention that may enable increased solubility, faster dissolution, increased bioavailability and targeting of resorption than a comparable dose of oxypurinol free acid.

In an aspect, provided is a pharmaceutical composition comprising a xanthine oxidase inhibitor and organic base that enhances or effects solubilisation of the xanthine oxidase inhibitor, and optionally a pharmaceutically acceptable carrier, excipient, vehicle or diluent.

In another aspect, provided is a pharmaceutical composition comprising a xanthine oxidase inhibitor and organic base that enhances or effects solubilisation of the xanthine oxidase inhibitor in an aqueous or organic solvent.

In a further aspect, disclosed is a liquid composition comprising a xanthine oxidase inhibitor and a solvent system which enhances or effects solubilisation of the xanthine oxidase inhibitor. Also disclosed is a drug comprising a liquid composition of a xanthine oxidase inhibitor and at least one organic base that is a solubilizing compound.

In a still further aspect, a composition is disclosed comprising a xanthine oxidase inhibitor and an organic base that is adapted for oral administration of the xanthine oxidase inhibitor.

Disclosed herein are compositions that may upon metabolism result in increased nitric oxide availability or bioavailability, by providing a metabolic substrate for nitric oxide production apart or in combination with decreased production of oxygen free radicals.

In a specific composition embodiment, the xanthine oxidase inhibitor and organic base may be in a ratio selected to augment the solubility of the xanthine oxidase inhibitor, augment the activity of the xanthine oxidase inhibitor, or provide a beneficial effect.

In a specific embodiment a basic amino acid is a subset of basic organic molecules.

Another aspect of embodiment is a specific ratio of xanthine oxidase inhibitor and organic base that increases solubility of xanthine oxidase inhibitor in aqueous solutions and or further improve or decreases the side effects associate with the administration of xanthine oxidase inhibitors. In another embodiment a molar ratio of XOI to organic base 1:0.01 to 1:100, more specifically 1:0.1 to 1:10.

An unique embodiment of the composition of xanthine oxidase inhibitor and organic base is improved or increased nitric oxide bioavailability in an animal or patient.

A further aspect, disclosed is that a powder mixture of xanthine oxidase inhibitor and basic amino acid increases aqueous solubility and bioavailability for oral administration accompanying an aqueous solution.

In an aspect of the disclosed is a composition of xanthine oxidase inhibitor and organic base that decreases the solubility of purines, xanthine, nuclei acids, or uric acid in an animal. In particular the organic base may decrease the solubility of purines or xanthine or nucleic acids or uric acid in situ in man.

One embodiment is a composition of xanthine oxidase inhibitor and organic molecule that when administered and metabolized provides a source of nitric oxide. More specifically, an organic molecule such as citrulline or arginine or organic molecule derived from citrulline or arginine, or pharmaceutically acceptable salt thereof.

In another embodiment, provided is a composition of a xanthine oxidase inhibitor and an organic base, in particular a liquid composition, that induces a decrease in hypertension, in new onset hypertension, pre-hypertension or hypertension, and/or improves systemic vascular resistance, reduces insulin resistance, decreases metabolic syndrome, delays, prevents or treats diabetes, delays, prevents or treats diabetic nephropathy, delays, prevents or treats diabetic retinopathy.

In a further embodiment, a composition, especially a liquid composition, is provided comprising a xanthine oxidase inhibitor and a basic amino acid, meglumine, tris (hydroxymethyl)-aminomethane, or choline.

Yet, another embodiment the composition of a xanthine oxidase inhibitor and organic molecule, where the organic molecule has a solubility in water of greater than 5 mg/ml.

In a specific embodiment the composition contains a xanthine oxidase inhibitor, an organic molecule and or other excipients. Where the organic molecule produces a basic solution upon exposure to aqueous solvent. A description of an organic base can be described as defined in the "Handbook of Pharmaceutical Salts, Properties, Selection and Use" P. Heinrich Stahl and Camille G Wermuth (Eds), Published by VHCA (Switzerland) and Wiley-VCH (FRG), 2011.

In a particular embodiment, a composition, especially a liquid composition, is provided comprising a xanthine oxidase inhibitor and a basic amino acid, in particular arginine or lysine or modified amino acid with basic properties in aqueous solution.

In certain embodiments, the xanthine oxidase inhibitor in a composition of the invention is allopurinol or oxypurinol, or febuxostat or pharmaceutically acceptable salts thereof. In particular, provided is a stable and substantially purified liquid composition comprising allopurinol or oxypurinol, more particularly oxypurinol, and an organic base, and optionally a pharmaceutically acceptable carrier, excipient, vehicle or diluent.

Also provided is a process for preparing xanthine oxidase inhibitor containing compositions. In a specific related aspect, the process for preparing a composition comprises one that includes allopurinol or oxypurinol and an organic base or bases, and, or other excipients.

In an embodiment, the invention describes a method of preparing a pharmaceutical composition comprising mixing a xanthine oxidase inhibitor (e.g. allopurinol or oxypurinol) and an organic base that enhances solubilization of the xanthine oxidase inhibitor, and optionally a pharmaceutically acceptable carrier, excipient, vehicle, or diluent.

A method of increasing aqueous solubility of a xanthine oxidase inhibitor is contemplated, comprising a xanthine oxidase inhibitor and an organic base that enhances or effects solubilization of the xanthine oxidase inhibitor. In an embodiment the organic base is a hydrotropic agent.

Compositions provided herein can be administered to a subject to treat or prevent a condition or disease which requires modulation of xanthine oxidase or which utilizes xanthine oxidase inhibitors to treat or prevent the condition or disease. (See for example, US patent publication 20080096904; 20100120796 or 20090130078. Therefore, the invention relates to a method for preventing or treating a condition or disease which requires modulation of xanthine oxidase or which utilizes xanthine oxidase inhibitors to treat or prevent the condition or disease comprising administering a therapeutically effective amount of a composition of the invention. Prophylactic and therapeutic methods are also provided comprising administering to a subject in need a therapeutically effective amount of a composition of the invention.

Pharmaceutical compositions provided herein may be adapted for administration to a subject in a number of ways. They may be administered in a convenient manner such as by oral and parenteral (e.g. intravenous, intraperitoneal, intramuscular, intraarticular, intrasternal, injection, infusion, and subcutaneous) routes.

As used herein, the terms "about" and "approximately" as used herein refer to values that are ±10% of the stated value.

The invention contemplates a method of administering a poorly soluble xanthine oxidase inhibitor to a subject in need thereof comprising administering a composition containing the xanthine oxidase inhibitor and an organic base that enhances or effects solubilization of the xanthine oxidase inhibitor.

The invention also contemplates the use of any of the compositions of the invention for preventing, and/or ameliorating disease severity, disease symptoms, and/or periodicity of recurrence of a condition or disease described herein.

The invention relates to the use of a xanthine oxidase inhibitor and an organic base in the preparation of a medicament for treating a condition or disease described herein.

Other objects, features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

DETAILED DESCRIPTION

Figure 1:
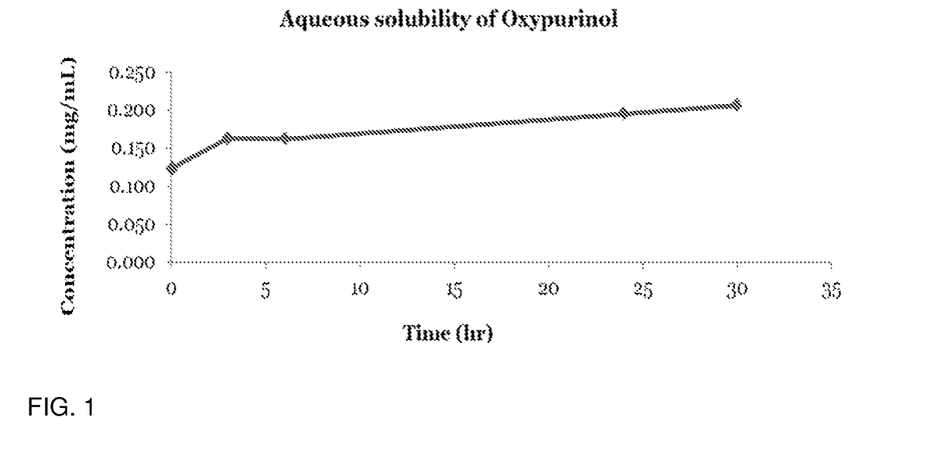
FIG. 1: Shows the equilibrium solubility, dissolution profile and solubility of oxypurinol free acid over a duration of 30 hours.
Figure 2:
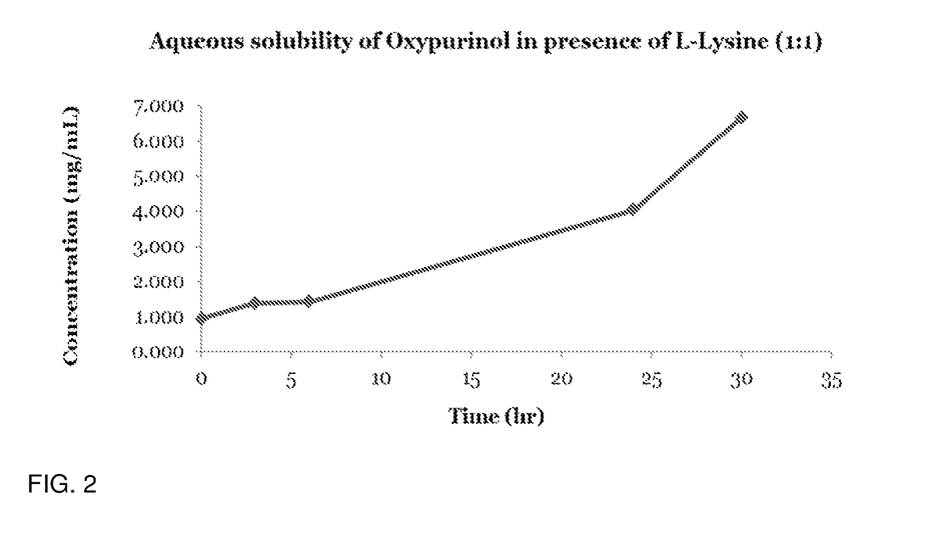
FIG. 2: Demonstrates the equilibrium solubility for increased dissolution and solubility of oxypurinol in aqueous solution in the presence of a 1 molar equivalent of lysine.
Figure 3:
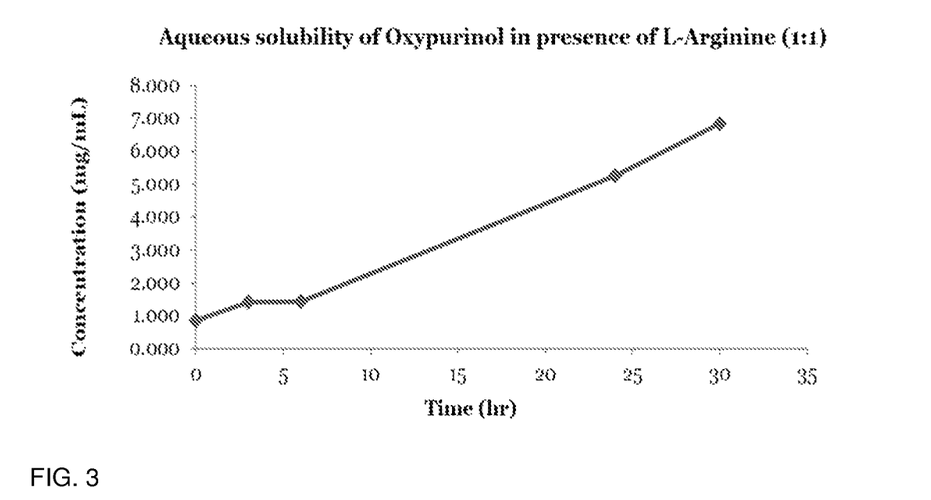
FIG. 3: Shows equilibrium solubility for oxypurinol, the increased dissolution and solubility of oxypurinol in the presence of a 1 molar equivalent of L-arginine.
Figure 4:
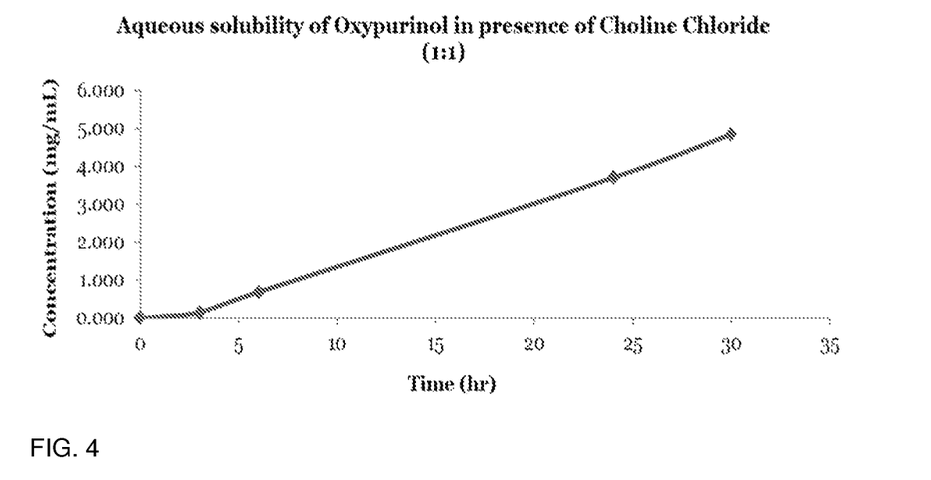
FIG. 4: shows the equilibrium solubility for increased dissolution of oxypurinol in choline. The evidence presented in FIGS. 2 and 3 show that an organic molecule with basic properties in aqueous solution may be advantageous for increasing XOI solubility compared to oxypurinol free acid FIG. 1 or neutral organic molecules such as choline.

Many xanthine oxidase inhibitors possess varied side effects and deficiencies that include nausea, gastrointestinal discomfort, dermal rash and poor bioavailability. Described herein is a liquid dosing formulation of xanthine oxidase inhibitor (XOI) that provides improvements to the side effects of XOI tablets. Also described herein is a composition that improves the dissolution and solubility of oxypurinol free acid when administered with an amino acid that is basic. Adolescents and geriatric patients often have difficulty taking tablet or solid forms and the liquid dosing formulation is considered to be more appealing to those sub populations of patients. Liquid dosing form comprises any one, any combination or all XOIs, and more specifically can be allopurinol, oxypurinol, 1-methylxanthine, or febuxostat, or powder that shows increased solubility of XOI compared to the free acid form. See FIGS. 1-4.

Accordingly, provided is a liquid dosing formulation for use with xanthine oxidase inhibitors that provides an improved side effect and pharmacokinetic profile for the treatment of health consequences related to hyperuricemia. The acidic environment of the stomach (Ph) may favor the formation of XOI crystal formation as may other compartments of gastrointestinal tract. It has been discovered that the solubility or bioavailability of XOIs can be enhanced without inducing adverse side effects typically experienced by XOIs in their convention form. In particular, formulations and liquid formulations, are provided that implement an organic base such as, but not limited to, basic amino acids, basic dipeptides, or basic tripeptides, which have neutralizing effect, thusly may decrease crystal formation of XOI's, purines, pyrimidine, xanthines and uric acid. Optionally, bicarbonate is an optional component and can serve to reduce urate crystal formation.

The term "amino acid" refers to naturally occurring and synthetic .alpha., .beta. .gamma. or .delta. amino acids, and includes but is not limited to, amino acids found in proteins, i.e. glycine, alanine, valine, leucine, isoleucine, methionine, phenylalanine, tryptophan, proline, serine, threonine, cysteine, tyrosine, asparagine, glutamine, aspartate, glutamate, lysine, arginine and histidine. In certain embodiments, the amino acid is in the L-configuration. Alternatively, the amino acid can be a derivative of alanyl, valinyl, leucinyl, isoleuccinyl, prolinyl, phenylalaninyl, tryptophanyl, methioninyl, glycinyl, serinyl, threoninyl, cysteinyl, tyrosinyl, asparaginyl, glutaminyl, aspartoyl, glutaroyl, lysinyl, argininyl, histidinyl, .beta.-alanyl, .beta.-valinyl, .beta.-leucinyl, .beta.-isoleuccinyl, .beta.-prolinyl, .beta.-phenylalaninyl, .beta.-tryptophanyl, .beta.-methioninyl, .beta.-glycinyl, .beta.-serinyl, .beta.-threoninyl, .beta.-cysteinyl, .beta.-tyrosinyl, . beta.-asparaginyl, .beta.-glutaminyl, .beta.-aspartoyl, .beta.-glutaroyl, .beta.-lysinyl, .beta.-argininyl or .beta.-histidinyl.

"Treating" or "treatment" of any disease or disorder refers, in certain embodiments, to ameliorating a disease or disorder that exists in a subject. In another embodiment, "treating" or "treatment" includes ameliorating at least one physical parameter, which may be indiscernible by the subject. In yet another embodiment, "treating" or "treatment" includes modulating the disease or disorder, either physically (e.g., stabilization of a discernible symptom) or physiologically (e.g., stabilization of a physical parameter) or both. In yet another embodiment. "treating" or "treatment" includes delaying the onset of the disease or disorder.

The term "modified amino acid" refers to an amino acid that is not a proteinogenic amino acid, or a post-translationally modified variant thereof. In particular, the term refers to an amino acid that is not one of the 20 common amino acids or pyrrolysine or selenocysteine, or post-translationally modified variants thereof.

"Xanthine oxidase inhibitor" refers to compounds that inhibit xanthine oxidase. Methods known in the art can be used to determine the ability of a compound to inhibit xanthine oxidase. (See for example the assay described in U.S. Pat. No. 6,191,136). A number of classes of compounds have been shown to be capable of inhibiting xanthine oxidase, and medicinal chemists are well aware of those compounds and manners in which they may be used for such purpose. It will be appreciated by the skilled artisan that xanthine oxidase inhibitors are numerous, and that the present invention may be carried out with any of the classes of pharmaceutically acceptable xanthine oxidase inhibitors. The disclosures of any patents and publications referenced herein are incorporated by reference. The nature and synthesis of the compounds are well taught in those patents and publications.

Functional derivatives of a xanthine oxidase inhibitor can be used in certain embodiments. "Functional derivative" refers to a compound that possesses a biological activity (either functional or structural) that is substantially similar to the biological activity of a xanthine oxidase inhibitor. The term "functional derivative" is intended to include "variants" "analogs" or "chemical derivatives" of a xanthine oxidase inhibitor. The term "variant" is meant to refer to a molecule substantially similar in structure and function to a xanthine oxidase inhibitor or a part thereof. A molecule is "substantially similar" to a xanthine oxidase inhibitor if both molecules have substantially similar structures or if both molecules possess similar biological activity. The term "analog" refers to a molecule substantially similar in function to a xanthine oxidase inhibitor. The term "chemical derivative" describes a molecule that contains additional chemical moieties which are not normally a part of the base molecule. A derivative may be a "physiological functional derivative" which includes but is not limited to a bioprecursor or "prodrug" which may be converted to a xanthine oxidase inhibitor.

The beneficial effects of the formulations provided are particularly evident with xanthine oxidase inhibitors that are poorly soluble. Poorly soluble may refer to a drug having a water solubility of less than about 200 µg/ml, more particularly 100 µg/ml at 37° C. A poorly soluble drug may also have a higher partition coefficient. The partition coefficient or distribution coefficient can be defined as log (Co/Cw) where Co and Cw are the equilibrium concentrations of the therapeutic in octanol and water. As used to herein, the terms "about" and "approximately" as used herein refer to values that are ±10% of the stated value.

A representative class of xanthine oxidase inhibitors for use in the compositions of the present invention are disclosed in U.S. Pat. Nos. 6,191,136 and 6,569,862, which are incorporated herein by reference. Compounds that are particularly useful include allopurinol (4-hydroxy-pyrazolo[3,4-d]pyrimidine) or oxypurinol (4,6-dihydroxypyrazolo[3,4-d]pyrimidine], or tautomeric forms thereof.

Xanthine oxidase inhibitors for use in the present invention can be synthesized by known procedures. Some therapeutic xanthine oxidase inhibitors also are commercially available, such as allopurinol, febuxostat and oxypurinol.

A xanthine oxidase inhibitor may be in a non-crystalline form, or a crystalline or amorphous form, or it may be a pharmaceutically acceptable salt of a xanthine oxidase inhibitor.

The term "organic base" refers to a hydrocarbon base. An organic base that enhances the solubility of a particular xanthine oxidase inhibitor may be selected for use in a composition of the invention. A pharmaceutically acceptable organic base is generally selected for use in the present invention.

The organic base can be a solubilizing compound that increases the aqueous solubility of a target xanthine oxidase inhibitor. A solubilizing compound may be a hydrotropic agent that increases the affinity of a target xanthine oxidase inhibitor for water. The concentration and/or solubility of a xanthine oxidase inhibitor in a composition of the invention can be greater in the presence of the hydrotropic agent than in its absence. A hydrotropic agent may be characterized by one or more of the following:

a) comprises at least one hydrophobic moiety;
   b) high water solubility (e.g. at least 2M);
   c) destabilizes water structure and at the same time interacts with a poorly soluble drug;
   d) at high concentrations solubilize a poorly soluble drug in water;
   e) self-associates and forms noncovalent planar or open-layer structures;
   f) nonreactive;

g) non-toxic; and/or h) does not produce any temperature effect when dissolved in water;

An organic base may be a Class 1, Class 2, or Class 3 organic base as described in the "Handbook of Pharmaceutical Salts, Properties, Selection and Use" P. Heinrich Stahl and Camille G Wermuth (Eds), Published by VHCA (Switzerland) and Wiley-VCH (FRG), 2011.

In specific embodiments, the organic base may be (a) a Class 1 base with a pKa1 between about 7 to 13 including but not limited to L-arginine, D-arginine, choline, L-lysine, D-lysine, and caffeine.

"Basic amino acids" include arginine, lysine, and ornithine. "Arginine" refers to the naturally occurring L-amino acid, any biochemical equivalents, and any precursors, basic forms, functionally equivalent analogs, and physiologically functional derivatives thereof. It includes sulfates of L-arginine, and sulfates of its functional analogs. Derivatives include peptides (i.e. poly L-arginine, arginine oligomers), other nitric oxide precursors such as homoarginine or substituted arginine such as hydroxyl-arginine. Therefore, suitable arginine compounds that may be used in the present invention include but are not limited to L-arginine, D-arginine, DL-arginine, L-homoarginine, and N-hydroxy-L-arginine, including their nitrosated and nitrosylated analogs (for example, nitrosated L-arginine, nitrosylated L-arginine, nitrosated N-hydroxy L-arginine, nitrosylated N-hydroxy-L-arginine, nitrosated L-homoarginine, and nitrosylated L-homoarginine, precursors of L-arginine and/or physiologically acceptable salts thereof, including for example, citrulline, ornithine, glutamine, lysine, polypeptides comprising at least one of these amino acids, and inhibitors of the enzyme arginase (e.g. N-hydroxy-L-arginine, and 2(S)-amino boronohexalioic acid). Naturally occurring sources include protamine. An arginine compound may be selected that lowers serum lipid.

"Lysine" refers to a naturally occurring L-amino acid any biochemical equivalents, and any precursors, basic forms, functionally equivalent analogs, and physiologically functional derivatives thereof. It includes sulfates of L-lysine, and sulfates of its functional analogs. Derivatives include peptides (i.e. poly L-lysine, lysine oligomers), other such as homolysine, L-N6-(1-iminoethyl)lysine derivatives, or substituted lysine such as methylated lysine, hydroxylysine, lysine substitituted with an N-epsilon-alkoxy or N-epsilon-alkenoxycarbonyl group, lysine substituted with a Nc-fluoroalkyloxycarbonyl or Nc-fluoroalkylsulphonyl group, lysine substituted with NX-(2-Nitropenylthio)-N-epsilon-acyl, or lysine substituted with a N-alkylsulphonyl or alkylaminocarbonyl group. Therefore, suitable lysine compounds that may be used in the present invention include but are not limited to L-lysine, D-lysine, DL-lysine, 6,6-dimethyl lysine, L-homolysine, and N-hydroxy-L-lysine, N-epsilon-2-hexyldecyloxycarbonyl-L-lysine, N-epsilon-2-decyltetradecyloxycarbonyl-L-lysine, N-epsilon-tetradecyloxycarbonyl-L-lysine, N-epsilon-2-hexadecyloxy-N-epsilon-2-hexyldecyloxycarbonyl-L-lysine, L-N6-(1-iminoethyl) lysine, N-epsilon-2-decyltetradecyloxycarbonyl-L-lysine, N-epsilon-tetradecyloxy-carbonyl-L-lysine, Nc-2-(F-octyl) ethyloxycarbonyl-L-lysine or Nc-2-(F-hexyl)ethyloxycarbonyl-L-lysine, N-epsilon-dodecylsulphonyl-L-lysine, N-epsilon-dodecylamino-carbonyl-L-lysine, including their nitrosated and nitrosylated analogs (for example, nitrosated L-lysine, nitrosylated L-lysine, nitrosated N-hydroxy L-lysine, nitrosylated N-hydroxy-L-lysine, nitrosated L-homo lysine, and nitrosylated L-homolysine, precursors of L-lysine and/or physiologically acceptable salts thereof. Lysine, and analogs and derivatives thereof may be prepared using methods known in the art or they may be obtained from commercial sources. For example, L-lysine is commercially produced utilizing gram positive *Corynebacterium glutamicum, Brevibacterium flavum* and *Brevibacterium lactofermentum* (Kleemann, A., et. al., "Amino Acids," in ULLMANN'S ENCYCLOPEDIA OF INDUSTRIAL CHEMISTRY, vol. A2, pp.57-97, Weinham: VCH-Verlagsgesellschaft (1985)), or mutant organisms.

A "condition" and/or "disease" contemplated herein refers to an indication that requires modulation of xanthine oxidase or which utilizes xanthine oxidase inhibitors to treat or prevent the condition or disease. In particular applications, the condition or disease is a cardiovascular disease and related diseases, hypertension, essential hypertension, hyperlipidemia, insulin resistance, metabolic syndrome, diabetes injury in tissues including the heart, lung, kidney, gastrointestinal tract, and brain, diabetes, inflammatory joint diseases such as rheumatoid arthritis, respiratory distress, kidney disease, renal dysfunction, liver disease, gout, hyperuricaemia, hyperlipidemia, hypercholesteremia, and conditions associated with excessive resorption of bone.

The invention provides compositions comprising xanthine oxidase inhibitors and an organic base that enhances or effects solubilisation of the xanthine oxidase inhibitor, and optionally a pharmaceutically acceptable carrier, excipient, vehicle or diluent. A xanthine oxidase inhibitor and organic base are preferably selected to ensure maximum solubility, bioavailability or activity of the xanthine oxidase inhibitor without increasing any side effects. Compositions of the invention especially include liquid compositions (e.g. solutions, syrups, colloids, or emulsions). Further, compositions of the invention contemplate micronized, lyophilized or dry-spray powders composed of XOI combined with one or more, organic molecules or organic bases or basic amino acid, that enhance the equilibrium solubility, dissolution or solubility, or bioavailability in an aqueous solution compared to oxypurinol free acid in water.

The invention contemplates a pharmaceutical composition comprising a unit dosage of at least one XOI and an organic base together with a pharmaceutically acceptable carrier, excipient, vehicle, or diluent. A "unit dosage" refers to a unitary i.e.

single dose, which comprises all the components of a composition of the invention, which is capable of being administered to a patient. A "unit dosage" may be readily handled and packed, remaining as a physically and chemically stable unit dose comprising the active agent and organic base with pharmaceutical carriers, excipients, vehicles, or diluents. In the alternative, a dosage form kit comprising a xanthine oxidase inhibitor and organic base, and the remaining components, are provided in separate containers, and the inhibitor and base, and remaining components, are combined prior to administration. In particular, a dosage form kit comprises a xanthine oxidase inhibitor and organic base in separate containers, and a solution for use is prepared by combining the ingredients with a suitable carrier, such as sterile water, prior to administration.

According to another embodiment, compositions are provided comprising a XOI, an organic base and/or choline, and an antioxidant. An antioxidant used for composition embodiments may include, but are not limited to, alpha lipoic acid, n-acetylcysteine, vitamin C.

Another embodiment relates to sterile dosage forms of a composition of the invention.

A formulation can be provided in a lyophilized form suitable for reconstitution and administration in a subject.

Also provided is a formulation where the XOI, organic base, and other ingredients of the composition are provided in a non-lyophilized or lyophilized form separate from each other. The ingredients can be reconstituted and/or solubilized in a suitable sterile liquid and combined to produce a pharmaceutical composition which is suitable for administration to a subject.

The compositions of the invention can have surprising physiochemical and pharmacological properties. The compositions may have one or more of the following characteristics: favorable equilibrium solubility, solubility, physiological compatible pH, enhanced stability, a long-lasting conservation, a better tolerability, and desirable physical properties (e.g. compression and flow properties) permitting the manufacture of a formulation useful for pharmaceutical medicinal purposes. Active xanthine oxidase inhibitor in a composition of the invention may be absorbed more rapidly and to a higher degree resulting in improved bioavailability. A composition of the invention may also be substantially non-toxic or have lower toxicity. Accordingly, the compositions of the invention, in particular the compositions comprising allopurinol and oxypurinol, are expected to be very useful as pharmaceutical agents as compared with previously described parent compounds and salts.

A composition of the invention can provide one or more beneficial effect. A beneficial effect can be improved safety, decreased side effects, enhanced biological, physical, and/or chemical properties or augmented desirable therapeutic effects of a xanthine oxidase inhibitor. Beneficial effects include but are not limited to increased absorption, distribution, metabolism and/or elimination of the xanthine oxidase inhibitor. The organic bases employed in the compositions can enhance the activity of the therapeutic composition, and/or provide the xanthine oxidase inhibitors in an active form while allowing facile application and administration for particular therapeutic purposes.

The beneficial effects may also be illustrated by increased serum levels of the active ingredients after administration as compared to the active ingredients alone. They may also be demonstrated by a decrease in serum uric acid levels. They may also be demonstrated by increased uric acid solubility, or increased nitric oxide bioavailability or decreased oxygen radical production in an animal, or specifically in man.

A composition of the invention can have increased bioavailability (absorbed more rapidly and to a higher degree) which can be illustrated by an increased equilibrium solubility, rate of dissolution and solubility in comparison to a xanthine oxidase inhibitor alone.

In one aspect, the rate of dissolution (i.e. mass of substance dissolved in a defined time period) of a xanthine oxidase inhibitor may be increased up to several fold in a composition of the invention when compared to the pure active substances. The solubility (i.e. mass of substance having dissolved clearly in a mass or certain volume of solvent) of a xanthine oxidase inhibitor contained in a composition of the invention may be increased giving rise to supersaturated solutions. An increase in terminal solubility may result which is maintained for at least several hours then decreasing to the solution's degree of saturation.

In an embodiment, provided is a composition with a resorption rate increased by a factor of 1.5, 2, 3, 4, 5, 10, 15, 20, and 50 when compared to the pure active substances.

The beneficial effects provided by a composition of the invention may be demonstrated as enhanced therapeutic effects.

In another embodiment, the invention provides a composition, especially a liquid composition, comprising a xanthine oxidase inhibitor that induces a decreased intracellular uric acid concentration. The decrease in circulating uric acid levels, or intracellular uric acid concentrations may represent at least about a 1%, 5%, 10%, 15%, 20%, 30%, 40%, 50%, 60%, 70% or, 1, 2, 3, 10, 30 or 100 fold decrease in circulating uric acid levels, or intracellular uric acid concentration in an in vitro uric acid assay or in vivo measurement of serum uric acid or intracellular or tissue uric acid.

In certain embodiments of compositions of the invention, the organic base is a solubilizing compound.

In other embodiments of the invention, the organic base is a hydrotropic agent, in particular a hydrotropic agent comprising a pyridine or benzene ring.

In particular embodiments of the invention, the organic base includes but is not limited to arginine, choline, L-lysine, D-lysine, glucamine and its N-mono- or N,N-disubstituted derivatives including but not limited to N-methylglucamine, N,N-dimethylglucamine, N-ethylglucamine, N-methyl,N-ethylglucamine, N,N-diethylglucamine, N-β-hydroxyethylglucamine, N-methyl,N-β-hydroxyethylglucamine, and N,N-di-β-hydroxyethylglucamine, benethamine, banzathine, betaine, deanol, diethylamine, 2-(diethylamino)-ethanol, hydrabamine, 4-(2-hydroxyethyl)-morpholine, 1-(2-hydroxyethyl)-pyrrolidine, tromethamine, diethanolamin(2,2"-iminobis(ethanol), ethanolamine (2-aminoethanol), 1H-imidazole, piperazine, triethanolamine (2,2',2"-nitrilotris(ethanol), N-methylmorpholine, N-ethylmorpholine, pyridine, dialkylanilines, diisopropylcyclohexylamine, tertiary amines (e.g. triethylamine, trimethylamine), diisopropylethylamine, dicyclohexylamine, N-methyl-D-glutamine, 4-pyrrolidinopyridine, dimethylaminopyridine (DMAP), piperidine, isopropylamine, or caffeine.

In another embodiment, the organic base is a basic amino acid, in particular lysine and arginine and the xanthine oxidase inhibitor is allopurinol or oxypurinol. In an embodiment, a liquid composition is provided comprising allopurinol or oxypurinol and L-arginine.

In a further embodiement, the composition of xanthine oxidase inhibitor and basic amino acid, may be administered as a powder to an animal or human subject, the enhanced solubility of the composition upon contact with water or other aqueous solution in the gastrointestinal track being sufficient to generate the liquid dosing form.

In a further embodiment, the invention provides compositions, especially liquid compositions comprising xanthine oxidase inhibitors and choline. Choline is a physiological compound which has been used in therapy and it does not suffer from disadvantages such as systemic or local toxicities.

An XOI and organic base can be in a ratio selected to augment the solubility of the XOI, augment the activity of the XOI, or provide a beneficial effect. The ratio of organic base to xanthine oxidase inhibitor can range from about 0.01 to 20.0 molar equivalent organic base to 1.0 molar equivalent of XOI. In an embodiment the ratio of organic base to XOI is 1.0:0.5 mole, in particular 1.0:1.0 mole, more particularly 1.0:3.0 mole.

A composition of the invention may also comprise a pharmaceutically acceptable carrier, excipient, vehicle, or diluent. A XOI and organic base can be mixed into a selected pharmaceutically acceptable carrier, excipient, vehicle, or diluent, and optionally other active ingredients including therapeutic agents are added.

The compositions of the present invention typically comprise suitable pharmaceutical carriers, excipients, vehicles, or diluents selected based on the intended form of administration, and consistent with conventional pharmaceutical practices. Suitable pharmaceutical carriers, excipients, vehicles, or diluents are described in the standard text, Remington's Pharmaceutical Sciences (Mack Publishing Company, Easton, Pa., USA 1985). By way of example, for oral administration in a liquid form, the drug components (i.e. XOI and organic base) may be combined with any oral, non-toxic, pharmaceutically acceptable inert carrier such as ethanol, glycerol, water, and the like. Suitable binders (e.g. gelatin, starch, corn sweeteners, natural sugars including glucose; natural and synthetic gums, and waxes), lubricants (e.g. sodium oleate, sodium stearate, magnesium stearate, sodium benzoate, sodium acetate, and sodium chloride), disintegrating agents (e.g. starch, methyl cellulose, agar, bentonite, and xanthan gum), flavoring agents, targeting agents, coloring agents, and other agents known to one skilled in the art, may also be combined in the compositions or components thereof.

In an embodiment, a composition of the invention is formulated so that it remains active at physiologic pH. The composition may be formulated in the pH range 4 to 10, in particular 5 to 9.

A composition for oral administration comprising a XOI and an organic base can be a liquid at temperatures ranging from about 15° C. to about 40° C., more particularly about 15° C. to about 30° C. The composition may contain at least about 0.1, 0.5, 1, 2, 3, 4, 5, 6, 7, 8, 9, 10, 11 or 12 mg/ml of solids.

In an aspect, the invention relates to an aqueous composition comprising a XOI of the invention and a solvent system which effects solubilization of the inhibitor. The solvent system effects solubilization of the inhibitor to provide an aqueous solution with beneficial properties for incorporation into an oral liquid formulation. The solvent system comprises an organic base, in particular arginine or lysine, more specifically arginine.

In an aspect, a liquid compositions may be prepared using an XOI, in particular allopurinol or oxypurinol and arginine, choline, glucamine (n-methylglucamine), or glucamine salts.

In an aspect, the invention provides a sterile, pyrogen-free, ready-to-use solution of a XOI, especially allopurinol or oxypurinol, which consists essentially of the XOI and organic base dissolved in a physiologically acceptable solvent therefore. In an embodiment, the solution has not been reconstituted from a lyophilizate.

The invention also provides an orally applicable composition comprising a XOI and organic base dissolved in a physiologically acceptable solvent therefor.

In a particular liquid composition of the invention comprising oxypurinol and arginine the concentration of oxypurinol is about 0.1-100 mg/ml, 0.5-50 mg/ml, 1-25 mg/ml, and 1-10 mg/ml, more preferably 10 mg/ml. The solution may be administered in a total volume of about 5 to 100 ml, preferably 30 ml, twice a day, to achieve the desired dose of about 200 to 1000 mg/day, preferably 600 mg/day. Alternatively, if a once-a-day dosing regimen is desired, the concentration of oxypurinol in the formulation may be about 6.0 to 60 mg/ml, preferably 20 mg/ml, administered in about 10 to 100 ml, preferably 30 ml of solution once a day.

Preferred liquid formulations of the invention comprise:
(1) allopurinol, oxypurinol, febuxostat or tautomers thereof in a concentration range of about 0.1 to about 100 mg/ml (w/v), more preferably about 0.5 to about 50 mg/ml (w/v), even more preferably about 1 to about 25 mg/ml (w/v), still more preferably about 1 to 10 mg/ml (w/v), and most preferably about 10 mg/ml;

(2) a basic amino acid having an appropriate concentration range to provide the suitable mole ratios of basic amino acid to XOIs; and
(3) a pharmaceutically acceptable diluent, preferably water, to bring the composition to a designated volume.

The preferable pH ranges for the solution formulation is from about pH 5.0 to about pH 10.0, preferably pH 7 to pH 10, and most preferably about pH 8.5 to 9.5.

Preferred embodiments of this aspect of the present invention include a composition formed by mixing:
(1) allopurinol, oxypurinol, febuxostat or tautomers thereof in a concentration of about 0.1 to about 100 mg/ml (w/v), more preferably about 0.5 to about 50 mg/ml (w/v), even more preferably about 1 to about 25 mg/ml (w/v), still more preferably about 1 to 10 mg/ml (w/v), and most preferably about 10 mg/ml
(2) arginine having an appropriate concentration range to provide the suitable mole ratios of basic amino acid to XOIs; and
(3) water as diluent.

In one embodiment, the solution formulation comprises a composition formed by mixing in no specified order:
(1) about 1 to 10 mg/ml of allopurinol, oxypurinol, or tautomers thereof;
(2) arginine having an appropriate concentration range to provide the suitable mole ratios of basic amino acid to XOIs; and
(3) water as a diluent, wherein the solution is at about pH 9 to 9.5 and is stored at about 20 to 30° C.

These liquid formulations can be maintained in the range of about pH 5.0 to about pH 10.0, and a pH of about 7-10 is most optimal for stabilizing the allopurinol, oxypurinol, or febuxostat or thereof.

The invention contemplates a lyophilized formulation as described herein. The lyophilization composition of the present invention can provides a product with increased stability, solubility or bioavailability. Lyophilized formulations of XOIs comprise: a XOI, an organic base, and a pharmaceutically acceptable carrier, excipient, or diluent. Storage conditions for the lyophilized formulation are typically at about 2° C. to about 25° C. XOIs with an organic base (e.g. arginine) can be lyophilized at a concentration of about 0.02 mg/ml to about 10 mg/ml of compound in the initial solution. A lyophilization solution preferably comprises (in addition to the XOs, an organic base, and a lyophilization buffer. The preferred pH range for the lyophilization buffer is from about 5.5 to about 12.0. A lyophilization buffer may contain sodium citrate, EDTA, and/or sucrose. A lyophilized xanthine oxidase formulation can be reconstituted in sterile water so as to maintain isotonic conditions of about 290 mOsm. The XOIs with organic base can be reconstituted in sterile water, optionally containing a stabilizing amount of antioxidants.

The present invention includes lyophilization cycles that yield a stable formulation. The lyophilization cycle is designed to keep the product below its collapse temperature during the primary drying phase. The moisture content can also be targeted to be less than 5%, preferably less than 2%.

The molar ratio of the reaction substrates oxypurinol free acid basic amino acid or di-peptide or tri-peptides or choline in the process is in the range 1:3, 1:2, 1:1.5, 1:1, 1:0.95, or 1:0.9 or any ratio in between the ranges indicated above.

Derivatives

According to certain embodiments, as used herein, derivatives of a compound (such as an XOI agent disclosed herein, e.g., allopurinol, oxypurinol, 1 methylxanthine, or febuxostat) include salts, esters, enol ethers, enol esters, acetals, ketals, orthoesters, hemiacetals, hemiketals, solvates, hydrates, metabolites or prodrugs thereof. Such derivatives may be readily prepared by those of skill in this art using known methods for such derivatization. The compounds produced may be administered to animals or humans without substantial toxic effects and either are pharmaceutically active or are prodrugs.

As used herein, solvent refers to any liquid that completely or partially dissolves a solid, liquid, or gaseous solute, resulting in a solution such as but not limited to hexane, benzene, toluene, diethyl ether, chloroform, ethyl acetate, dichloromethane, carbon tetrachloride, 1,4-dioxane, tetrahydrofuran, glyme, diglyme, acetone, acetonitrile, dimethylformamide, dimethyl sulfoxide, dimethylacetamide, or N-methyl-2-pyrrolidone.

It is to be understood that reactants, compounds, solvents, acids, bases, catalysts, agents, reactive groups, or the like may be added individually, simultaneously, separately, and in any order. Furthermore, it is to be understood that reactants, compounds, acids, bases, catalysts, agents, reactive groups, or the like may be pre-dissolved in solution and added as a solution (including, but not limited to, aqueous solutions). In addition, it is to be understood that reactants, compounds, solvents, acids, bases, catalysts, agents, reactive groups, or the like may be in any molar ratio.

It is to be understood that reactants, compounds, solvents, acids, bases, catalysts, agents, reactive groups, or the like may be formed in situ.

Solvates

The XOI agents also includes solvate forms of the agents. The terms used in the claims encompass these forms.

Polymorphs

The XOI agents also include their various crystalline forms, polymorphic forms and (an)hydrous forms. It is well established within the pharmaceutical industry that chemical compounds may be isolated in any of such forms by slightly varying the method of purification and or isolation form the solvents used in the synthetic preparation of such compounds.

Prodrugs

Embodiments of the disclosure further include XOI agents in prodrug form. Such prodrugs are generally compounds wherein one or more appropriate groups have been modified such that the modification may be reversed upon administration to a human or mammalian subject. Such reversion is usually performed by an enzyme naturally present in such subject, though it is possible for a second agent to be administered together with such a prodrug in order to perform the reversion in vivo. Examples of such modifications include ester (for example, any of those described above), wherein the reversion may be carried out be an esterase etc. Other such systems will be well known to those skilled in the art.

Applications

The compositions of the invention may be used to prevent or treat conditions or diseases which require modulation of xanthine oxidase, which utilize XOIs to prevent or treat the condition or disease, or which are treatable using a XOI. Therefore, the invention relates to a method for preventing or treating in a subject a condition or disease which requires modulation of xanthine oxidase or which utilize XOIs to prevent or treat the condition or disease comprising administering a therapeutically effective amount of a composition of the invention.

As used herein, by the term "effective amount," "amount effective," "therapeutically effective amount," or the like, it is meant an amount effective at dosages and for periods of time necessary to achieve the desired result, e.g., inhibit xanthine oxidase, lower uric acid, treat a disease or medical condition associated with elevated uric acid levels, requires modulation of xanthine oxidase or is treated with an XOI. Elevated uric acid levels typically relate to level above 5.5 mg/dl.

The compositions of the invention provide a useful means for administering active XOIs to subjects suffering from a condition or disease.

The compositions of the invention provide a useful means for administering active XOI's to subjects suffering from one or all of, obesity, hypercholestremia, hyperlipidemia, hyperuricemia, fatty liver disease, chronic kidney disease, end stage renal disease, or diabetic nephropathy.

A pharmaceutical composition of the invention may provide advantageous effects in the treatment of conditions or diseases of varied body systems, such as heart, kidney, or cardiovascular disease or related diseases, diseases of the brain, diabetes, inflammatory joint diseases such as rheumatoid arthritis, inflammatory conditions or diseases, respiratory distress, liver disease, sepsis, burns, gout, hyperuricaemia, and conditions associated with excessive resorption of bone. In particular applications the condition or disease is hypertension, insulin resistance, metabolic syndrome, kidney injury, glomerular sclerosis, diabetic nephropathy, diabetes, diabetic blindness, diabetic ischemic injury, hypertrophy, congestive heart failure subsequent to myocardial infarction, myocardial ischemia, myocardial infarction, and diseases that arise from thrombotic and prothrombotic states in which the coagulation cascade is activated.

The compositions of the invention, especially the liquid formulations, can be readily adapted to a therapeutic use in the treatment of cardiovascular and related diseases. Thus, the invention contemplates the use of a composition of the invention for preventing, and/or ameliorating disease severity, disease symptoms, and/or periodicity of recurrence of a cardiovascular or related disease.

The invention provides a pharmaceutical composition, especially a liquid composition, for the treatment of hypertension, insulin resistance, metabolic syndrome, kidney injury, glomerular sclerosis, diabetic nephropathy, diabetes, diabetic blindness, diabetic ischemic injury, congestive heart failure comprising a congestive heart failure amount of a XOI, an organic base, and a pharmaceutically acceptable carrier, excipient, vehicle, or diluent. In an embodiment, the organic base is a basic amino acid and the xanthine oxidase inhibitor is allopurinol or oxypurinol, or febuxostat which is directed to preventing or treating cardiovascular and related diseases.

EXAMPLES

Example 1

Tables 1 and 2 respectively, show compositions of syrup and powder for solution or suspension formulations comprised of a serum uric acid lowering agent (active pharmaceutical ingredient), allopurinol and/or oxypurinol, and one or more of the functional (active or inactive) and non-functional excipients within the ranges specified. The ranges of active ingredients are based on the adult daily tolerable upper intake limit or highest adult daily dose described in a Health Canada Monograph. The percentages for non-functional excipients are based on commonly observed levels in FDA approved marketed products of similar use.

TABLE 1

Compositions of syrup formulation for allopurinol or oxypurinol, presented in a multi-dose bottle. The formulation includes an active pharmaceutical ingredient (API), either allopurinol or oxypurinol and one or more of the functional and non-functional excipients listed in Table 1. The dose is administered either once or multiple times daily; however, the maximum daily dose range is not to be exceeded. Hence, for multi-dose administration, individual dose volumes will depend on final concentrations of components in the presentation.

| Component | | Range |
|---|---|---|
| Active pharmaceutical ingredient | allopurinol or | 0-800 mg[1] |
| | Oxypurinol Or | 0-800 mg[2] |
| | Febusoxtat | 0-800 mg[2] |
| Other active (functional excipients) and inactive pharmaceutical ingredients | | |
| Excipient(s) | L-arginine | 0-3 grams[3] |
| | L-lysine[5] | 0-3 grams[3] |
| | folic acid (vitamin B9) | 0-1000 micrograms[4] |
| | choline chloride | 0-3.5 grams[4] |
| | niacin or niacinamide (vitamin B3)[5] | 0-35 milligrams[4] |
| | pyridoxine HCl (vitamin B6) | 0-100 milligrams[4] |
| | riboflavin (vitamin B2)[5] | 0-100 milligrams[3] |
| | thiamine (vitamin B1) | 0-100 milligrams[3] |
| | cyanocobalamin (vitamin B12) | 0-1000 micrograms[3] |
| | calcium pantothenate (vitamin B5) | 0-500 milligrams[3] |
| | biotin (vitamin B7) | 0-500 micrograms[3] |
| | L-ascorbic acid (vitamin C)[5] | 0-2000 milligrams[4] |
| | cholecalciferol (vitamin D3) | 0-100 micrograms[4] |
| Non-Functional Excipients/Processing Aids | | |
| | sweetener (e.g. sucralose5, stevia-rebaudioside A is active ingredient, approved as a dietary supplement) | 0-2% |
| | Emulsifier/wetting agents (e.g. xanthan gum. Hypromelloses, povidones) | 0-10% of each as required |
| | basic pH modifier (e.g. sodium, potassium, magnesium salts of (bi)carbonate, phosphate or hydroxide or magnesium oxide) | 0-5% of each as required |
| | flavouring (e.g. tutti frutti) | 0-2% |
| | preservative (e.g. ascorbic acid or sodium benzoate) | 0-5% |
| | Colour (e.g. titanium dioxide, sunset yellow) | 0-0.005% |

TABLE 2

Compositions of a powder for solution or powder for suspension, presented in single dose sachet format for allopurinol or oxypurinol. The formulation may or may not be effervescent or gelatin capsule and is to be taken either once, twice or three times a day depending on body weight. The single dose sachet contains an active pharmaceutical ingredient (API), allopurinol and/or or oxypurinol and one or more of the functional and non-functional excipients listed in Table 2.

| Component | | Range |
|---|---|---|
| Active pharmaceutical ingredient | allopurinol or | 0-800 mg[1] |
| | oxypurinol | 0-800 mg[2] |
| Other active (functional excipients) and inactive pharmaceutical ingredients | | |
| Excipient(s) | L-arginine | 0-3 grams[3] |
| | L-lysine[5] | 0-3 grams[3] |
| | folic acid (vitamin B9) | 0-1000 micrograms[4] |
| | choline chloride | 0-3.5 gram[4] |
| | niacinamide (vitamin B3)[5] | 0-35 milligrams[4] |
| | pyridoxine HCl (vitamin B6) | 0-100 milligrams[4] |
| | riboflavin (vitamin B2)[5] | 0-100 milligrams[3] |
| | thiamine (vitamin B1) | 0-100 milligrams[3] |
| | cyanocobalamin (vitamin B12) | 0-1000 micrograms[3] |
| | calcium pantothenate (vitamin B5) | 0-500 milligrams[3] |
| | biotin (vitamin B7) | 0-500 micrograms[3] |
| | L-ascorbic acid (vitamin C) | 0-2000 milligrams[4] |
| | cholecalciferol (vitamin D3) | 0-100 micrograms[4] |
| | sweetener (e.g. sucralose, stevia) | |
| Non-Functional Excipients/Processing Aids | | |
| | basic pH modifier/effervescent agent (e.g. sodium, potassium, magnesium salts of (bi)carbonate, phosphate or hydroxide or magnesium oxide) | 0-5% of each as required |
| | Emulsifier/wetting agents,suspending agents (e.g. xanthan gum, hypromelloses, povidones) | 0-10% |
| | sweetener (e.g. sucralose5, stevia-rebaudioside A is active ingredient, approved as a dietary supplement) | 0-2% |
| | flavouring (e.g. tutti frutti) | 0-2% |
| | Disintegrant/filler/glidants (e.g. silicon dioxide, magnesium stearate,) | 0-15% each as required |
| | Colour (e.g. titanium dioxide, sunset yellow) | 0-0.005% |

For once a day dosing, a single sachet or gelatin capsule would be administered containing a formulation with no more than the maximum daily dose as listed for each active and excipient component in Table 2. For a twice daily dosing presentation, single units of the maximum composition range, divided by two would be prepared and administered. For three times a day dosing, single dose unit presentations containing no more than one third of the maximum range of each component would be prepared.

REFERENCES

1. Chao J, Terkeltaub R. A Critical Reappraisal of Allopurinol Dosing, Safety, and Efficacy for Hyperuricemia in Gout. Current Rheumatology Reports 2009, 11:135-140
2. NDA 21-740-OXYPRIM™, Arthritis Advisory Committee Briefing Document (Jun. 2, 2004) at www.fda.gov 3. Health Canada Monographs at www.hc-sc.gc.ca
4. National Academy of Sciences Dietary Reference Intakes
5. On FDA's list of inactive ingredients of approved drugs Example 2

A Dual Sachet Presentation

One sachet containing the drug as a powder with the necessary excipients to ensure it dissolves either as an effervescent solution in water or not and may or may not include the amino acid(s) to enhance solubility (this is powder for solution or suspension depending on solubility) and a second sachet containing the dietary components as a powder. Administration would involve the patient opening each pack and dissolving both tablets simultaneously in water (or juice) and drinking within a prescribed period of time.

Example 3

Sachet Tablets

Alternatively, the components of both sachets of Example 2 could contain disintegrating tablets that would be dissolved simultaneously in water (or juice) for administration as previously described.

Example 4

Sachet Tablets

Another option would be to consider presentation of the two disintegrating tablets (active and dietary supplements) in one sachet for dissolution in a liquid for administration. Excipient ranges for allopurinol- or oxypurinol or febuxostat or other xanthine oxidase inhibitor oral liquid formulations are described herein.

Example 5

Micronized Dry Mixture

Still another choice would be a dry mixture of oxypurinol or allopurinol, combined with a basic amino acid, micronized with sufficiently controlled particle size that would beneficially affect aqueous dissolution or solubility or bioavailability or all of the aforementioned properties. Delivery of this composition mixture is envisioned in sachet, gelatin capsule, or tablet.

REFERENCES

1. Cannon P J, et al Hyperuricemia in primary and renal hypertension, N Engl J Med 1966; 275:457-64
2. Ford E S, et al., Serum concentrations of uric acid and the metabolic syndrome among children and adolescents. Circulation 2007; 115:2526-32
3. Siu Y P, et al., The use of allopurinol in slowing the progression of renal disease through it's ability to lower serum uric acid level. Am J Kidney Dis 2006; 47:51-9
4. Nakagawa et al, Am J Physiol 2006; 290:F625-631
5. J Hypertens 2010; 28: 1234-42
6. Pachla L A, Kissinger P T. Measurement of serum uric acid by liquid chromatography. Clin Chem 1979; 25:1847-1852.
7. Ismail A A A, Dakin T A. Gas chromatography and characterization of tetraethyl derivatives of uric acid. J Chromatogr 1975; 110:182-186.
8. Milner J A, Perkins E G. Determination of uric acid in biological fluids by high performance liquid chromatography. Anal Biochem 1978; 88:560-565.
9. Ellerbe P, Cohen A, Welch M J, White V E. The stability of uric acid in ammonium hydroxide. Clin Chem 1988; 34:2280-2282.

It should be borne in mind that all patents, patent applications, patent publications, technical publications, scientific publications, and other references referenced herein and in the accompanying appendices are hereby incorporated by reference in this application to the extent not inconsistent with the teachings herein.

It is important to an understanding to note that all technical and scientific terms used herein, unless defined herein, are intended to have the same meaning as commonly understood by one of ordinary skill in the art. The techniques employed herein are also those that are known to one of ordinary skill in the art, unless stated otherwise. For purposes of more clearly facilitating an understanding the invention as disclosed and claimed herein, the following definitions are provided.

While a number of embodiments have been shown and described herein in the present context, such embodiments are provided by way of example only, and not of limitation. Numerous variations, changes and substitutions will occur to those of skilled in the art without materially departing from the invention herein. For example, the present invention need not be limited to best mode disclosed herein, since other applications can equally benefit from the teachings. Also, in the claims, means-plus-function and step-plus-function clauses are intended to cover the structures and acts, respectively, described herein as performing the recited function and not only structural equivalents or act equivalents, but also equivalent structures or equivalent acts, respectively. Accordingly, all such modifications are intended to be included within the scope of this invention as defined in the following claims, in accordance with relevant law as to their interpretation.

What is claimed is:

1. A composition comprising oxypurinol and L-arginine, wherein (i) the molar ratio of oxypurinol to L-arginine is about 1:1 to about 1:10; (ii) the oxypurinol and L-arginine, are in powder form; and (iii) the composition comprises 200 mg-1000 mg of oxypurinol.

2. The composition of claim 1, further comprising bicarbonate or carbonate or salts thereof.

3. The composition of claim 1, further comprising an artificial or natural sweetening agent.

4. The composition of claim 1, further comprising a coloring agent.

5. The composition of claim 1, further comprising an antioxidant.

6. The composition of claim 1, further comprising a vitamin.

7. The composition of claim 6, wherein said vitamin is C, B1,B6,B12, or D.

8. The composition of claim 6, wherein said vitamin is not niacin.

9. The composition of claim 1 further comprising methyl cellulose.

10. The composition of claim 9, wherein said methyl cellulose is present at between 0.1 to 3 percent, by weight.

11. The composition of claim 1, wherein the molar ratio of oxypurinol to L-arginine, about 1:1 to about 1:2.

* * * * *